US007651759B2

(12) United States Patent
Lahti et al.

(10) Patent No.: US 7,651,759 B2
(45) **Date of Patent: *Jan. 26, 2010**

(54) DIGITAL PRINTING METHOD AND A PAPER OR BOARD APPLICABLE THERETO

(75) Inventors: Johanna Lahti, Pori (FI); Tapani Penttinen, Huutjärvi (FI); Jari Räsänen, Imatra (FI); Jurkka Kuusipalo, Tampere (FI); Antti Savolainen, Kangasala (FI)

(73) Assignee: Stora Enso Oyj, Helsinki (FI)

( * ) Notice: Subject to any disclaimer, the term of this patent is extended or adjusted under 35 U.S.C. 154(b) by 70 days.

This patent is subject to a terminal disclaimer.

(21) Appl. No.: 11/724,538

(22) Filed: Mar. 15, 2007

(65) Prior Publication Data

US 2007/0202308 A1 Aug. 30, 2007

Related U.S. Application Data

(63) Continuation of application No. 10/497,954, filed on May 3, 2005.

(51) Int. Cl.
*A61F 13/15* (2006.01)

(52) U.S. Cl. .................... 428/219; 428/195.1; 428/500; 428/512; 428/537.5; 428/207; 428/211.1; 428/213; 428/220; 428/332; 428/337; 428/341; 428/342; 428/511; 346/135.1; 346/141; 430/124.1

(58) Field of Classification Search .............. 428/195.1, 428/207, 211.1, 213, 219, 220, 332, 337, 428/341, 342, 500, 511, 537.5, 512; 346/135.1, 346/141; 430/124.1
See application file for complete search history.

(56) References Cited

U.S. PATENT DOCUMENTS 3,481,775 A * 12/1969 Albertson ................... 428/486
4,820,557 A 4/1989 Warren
4,915,299 A 4/1990 Harkus
5,026,600 A 6/1991 Akao
5,075,163 A 12/1991 Akao
5,741,572 A 4/1998 Heeg et al.

(Continued)

FOREIGN PATENT DOCUMENTS

EP 0 629 930 B1 5/1998

(Continued)

*Primary Examiner*—Betelhem Shewareged
(74) *Attorney, Agent, or Firm*—Patterson, Thuente, Skaar & Christensen, P.A.

(57) ABSTRACT

The invention relates to a digital printing method and a paper or board applicable thereto. In digital printing, the surface of a paper or board is charged electrically, toner particles are brought to the surface in an electric field in accordance with the printing, and the particles are melted fast to the surface with the help of heat for forming the printing. According to the invention, the paper or board (2) is provided with a coating layer (3) containing an electrically chargeable acrylate copolymer of ethylene, which receives the toner that is fused to the coating with the help of infra red radiation. Suitable coating polymers are especially methyl, ethyl and butyl acrylate copolymers of ethylene (EMA, EEA and EBA). Especially in packaging boards, besides the digitally printable layer, the polymer coatings can comprise a water vapour or oxygen barrier layer for protecting the packed product, and a heat-sealable layer on the opposite side of the board for sealing the package.

17 Claims, 2 Drawing Sheets

U.S. PATENT DOCUMENTS

| | | | |
|---|---|---|---|
| 5,789,123 A | | 8/1998 | Cleckner et al. |
| 5,840,385 A | | 11/1998 | Penttinen et al. |
| 5,858,516 A | * | 1/1999 | Ou-Yang ................. 428/195.1 |
| 5,942,295 A | * | 8/1999 | Adur et al. ................. 428/34.2 |
| 6,042,985 A | | 3/2000 | Matsuda et al. |
| 6,051,305 A | | 4/2000 | Hsu |
| 6,102,536 A | | 8/2000 | Jennel |
| 6,156,416 A | | 12/2000 | Daems et al. |
| 6,231,953 B1 | | 5/2001 | Mossbrook et al. |
| 6,316,120 B1 | | 11/2001 | Emslander |
| 2004/0213970 A1 | | 10/2004 | Knauf |
| 2005/0175817 A1 | | 8/2005 | Lahti |
| 2005/0235611 A1 | | 10/2005 | Roussos |

FOREIGN PATENT DOCUMENTS

| | | |
|---|---|---|
| EP | 0 845 711 B1 | 10/2000 |
| WO | WO 98/49605 | 11/1998 |
| WO | WO 99/59029 | 11/1999 |
| WO | WO 00/01536 | 1/2000 |

* cited by examiner

DIGITAL PRINTING METHOD AND A PAPER OR BOARD APPLICABLE THERETO

CROSS REFERENCE TO RELATED APPLICATION

This application is a Continuation of U.S. application Ser. No. 10/497,954 entitled "A Digital Printing Method and a Paper or Board Applicable Thereto" filed on May 3, 2005, which is hereby incorporated by reference in its entirety herein, and on which priority is based.

The present invention relates to a digital printing method, in which the surface of paper or board is charged electrically, toner particles are brought to the surface in an electric field in accordance with the printing, and the particles are fused to the surface with the help of heat for forming the printing. In addition, the invention relates to a polymer-coated paper or board applicable to the method, and to the use of selected polymers in the coating.

BACKGROUND OF THE INVENTION

Digital printing is known as a technique, and it is widely used, among others, in colour printing, copying machines and printers. The application EP 629930 discloses a digital printing technique, with which a multi-colour printing is achievable on one side or both sides of a moving paper web. The different shares of the printing are produced in successive printing stations along the path of the web, the printing stations being arranged to operate in a synchronised way. Each station comprises a rotating drum, with an accumulator installed on its periphery, producing a uniform electric charge to the surface of the drum. On the periphery of the drum, the accumulator is followed by a printhead, such as a laser scanner, which forms a latent image to the surface of the drum by selectively changing the charge of the drum surface, the latent image being then developed in a developing station, in which opposite signed toner particles are brought to the surface of the drum in accordance with the image. After this, the surface of the drum is brought into contact with the paper web led past it for transferring the toner particles forming the image to the surface of the web. For this purpose, in the point of contact of the drum and the web, a corona transfer assembly has been installed on the opposite side of the web, the electric current directed through which forming an electric field, which draws the electrically charged toner particles from the surface of the drum to the surface of the paper web. Immediately adjacent to the corona transfer assembly there is installed an alternating-current corona apparatus, which eliminates the charges of the web and allows it to separate from the surface of the drum. The surface of the drum is then pre-charged by the corona apparatus and cleaned from the toner particles possibly remaining on it, after which the surface is ready for a new printing cycle, which may as well be identical with the previous cycle as be different from it.

Black-and-white printing can be produced on the one side of the paper in one single printing station using black toner in a way disclosed above. In multi-colour printing, the different toners are brought to the paper in several successive printing stations which operate with different colours, adding them to the printing to be generated to the moving web one at a time. The printing of both sides of the paper can still be achieved by placing printing stations of the type disclosed above to both sides of the moving paper web.

After the printing consisting of one or more toners is produced onto the paper as disclosed above, the printing is fixed in a fixing station located on the path of the web. The fixing is performed using infrared radiators, which heat the surface of the web so that polymeric toner particles melt fast to the paper. Finally, the finished printed web is cut to sheets, which are piled or stitched, according to the need of any given time.

An essentially corresponding technique is applied to copying machines and printers, in which the printing base is formed of individual sheets, instead of a continuous web. In addition to paper sheets, also plastic films can be used as a base in copying machines.

In the printed patent specification U.S. Pat. No. 5,741,572, there is disclosed a paper intended to be printed electrophotographically, which is coated with ionomer (Surlyn 1605) or a mixture of ionomer and some other polymer. For the toner to be fixed with the help of heat, the specification likewise suggests ionomer to be used. According to the specification, ionomer resins do not tend to spread, due to which the print lasts well during and after thermal fixing.

The drawback of digital printing technique in the printing of board webs has been the typically more irregular surface of the boards, which causes a printing result of poor quality. Boards have been printed using conventional printing techniques, such as offset printing. Especially polymer coated packaging boards used for packages and disposable dishes can have been printed before the coating phase, in which case coating layers consisting of colourless or transparent polymers have been extruded onto the board surface provided with printings, or offset printing can have been performed onto a board pre-coated with polymer.

SUMMARY OF THE INVENTION

According to the present invention it has been noted that bringing a polymer coating onto a paper or board with rough surface evens out the irregularities of the surface so that, for this part, the obstacles for its successful digital printing are removed. However, tests have revealed that the result is strongly dependent on the polymer used in the printing. Different polymers namely produce impressions of a very different quality.

Researches carried out indicate that the quality of the printing clearly correlates with how evenly the polymer is charged in the corona treatment. According to test results, polar acrylate copolymer of ethylene, namely ethylene-methyl-acrylate co-polymer (EMA) was charged very evenly in the corona treatment and produced a high-quality impression in digital printing.

Thus, it is characteristic of the digital printing method of the invention that the printing is performed onto a polymer coated paper or board, in which the coating contains electrically chargeable acrylate copolymer of ethylene, by charging the surface of paper or board electrically, by bringing toner particles to the surface in an electric field in accordance with the printing, and by directing infrared radiation to the points of printing on the surface, the infrared radiation fusing the toner fast to the polymer coating with the help of heat.

Electrically chargeable acrylate copolymers of ethylene applicable in the invention are especially ethylene methyl acrylate copolymer (EMA), and ethyl butyl acrylate (EBA) and ethylene ethyl acrylate (EEA) copolymers, which have similar characteristics as EMA.

In addition to digital printability, the advantages of electrically chargeable acrylate copolymers of ethylene as the coating polymer of paper or board to be printed are their extrudability and adhesiveness both to paper and board and to other extrudable polymers generally used in the coating of packaging boards. A digitally printable polymer layer can thus be part of the multi-layer coating to be extruded onto paper or board. The polymers used, such as EMA, EEA and EBA, are also heat-sealing, so also in this respect, they are suitable as the surface layer of a board to be used for sealable packages. Further, it has been observed that the EMA surface does not become matted when fixing the toner particles by IR radiation. After the printing, i.e. the fusing of the toner, protective lacquer can be spread onto the printing surfaces, with the exception of areas to be heat sealed, the protective lacquer adhering smoothly to the ethylene copolymers.

EMA is manufactured by copolymerisation of ethylene and methyl acrylate monomers, the share of the latter in commercial EMA products being between 9-20 mole percent. As the share of methyl acrylate increases, the impression improves, but at the same time, the polymer becomes softer and more viscous. As the EMA layer is brought to the surface of paper or board, the share of methyl acrylate monomer in EMA is preferably between 15-20 mole percent, and most preferably approx. 15 mole percent, in which case paper or board can be rolled without adhesion problems caused by the coating.

It is characteristic of the digitally printable polymer coated paper or board that the fibre base has one or more coating layers so that, for the essential part, the uppermost layer consists of an acrylate copolymer of ethylene, especially ethylene methyl acrylate copolymer (EMA).

The above expression "for the essential part" refers to that the polymer layer on paper or board is either pure commercially available EMA, or only small amounts of other components (below 10% and, more preferably, below 5%) have been mixed with it, which do not substantially influence the charging of the polymer in corona treatment nor the quality of the digital print.

A simple and advantageous embodiment of the invention is that the polymer coating on the fibre base of paper or board only comprises one EMA layer. Such a coating layer can also be located only on one side of paper or board. For example, digitally printed box packages for demanding purposes, such as packages for cosmetics or other luxury products, can be manufactured of such a simple coated packaging board. One-side polymer coating renders such dry packages a sufficient protection against wetting from the outside.

The paper or board of the invention, coated with EMA on both sides, is again suitable, for example, for multi-colour printed advertising leaflets, brochures or cards.

According to the invention, due to its adhesiveness, EMA can also be part of a multi-layer coating brought onto paper or board, in which, in addition to digital printability, also water vapour and oxygen barrier especially required from food packages, or as good heat-sealability as possible, has been searched for. Thus, the other layers of the coating can consist of barrier polymers, such as ethyl vinyl alcohol copolymer (EVOH) or polyamide (PA), or low-density polyethylene (LDPE) used especially as heat-sealing polymer, or polypropylene (PP). The EVOH and PA layers are most preferably located against the board below the EMA layer, as again the LDPE layer is located on the opposite side in relation to the printable side of the board.

The toner particles typically contain polymers with a low melting point so that they melt easily by the action of IR radiation. The toner particles can thus be melted and fused with the coating without the melting of the coating polymer. Alternatively, IR radiation can soften or melt the polymer coating so that, as the result, the toner particles adhere to the coating without melting the toner particles themselves. The most effective fusion is achieved if both the coating and the toner particles melt by the action of IR radiation.

Besides the electric chargeability, the setting of the toner onto the printing surface is based on the polarity of the toner particles. In other respects, the polymer being the base for the toner is not a critical matter for the invention; in other words, the coating and the toner can contain the same polymer or they can contain polymers of different types.

The objects of the invention further comprise the use of an acrylate copolymer of ethylene, such as EMA, in the polymer coating receiving the toner of the digitally printable coated paper or board. In this case, EMA is most preferably used as a substantially pure material layer consisting of it, which can by itself form the polymer coating of the paper or board on one side or both sides, or it can form one, the outermost layer of the multi-colour coating on the paper or board.

The invention is next explained in more detail with the help of examples, referring first to the enclosed drawings, in which

BRIEF DESCRIPTION OF THE FIGURES

In FIG. 1, there is shown a simple polymer coated digitally printable packaging board 1 according to the invention, the one side of the fibre base 2 of which contains the coating layer 3 consisting substantially of pure EMA. The fibre base 2 can be formed of a three-layer structure comprising an inner layer of chemithermomechanical pulp (CTMP) and outermost layers of sulphate pulp, the weight of the three-layer structure being 130-600 g/m$^2$, preferably 170-300 g/m . The polymer of the EMA layer 3 is formed by copolymerising ethylene and methyl acrylate monomers so that the share of methyl acrylate monomer of the monomer mixture is 9-20 mole percent, most preferably about 15-20 mole percent. The weight of the EMA layer can be 7-20 g/m$^2$.

FIG. 2 shows the polymer coated digitally printable paper 4 of the invention, in which the weight of the paper layer 5 forming the fibre base is 20-130 g/m$^2$, preferably 40-120 g/m$^2$. The EMA layer 3 used as the coating can be similar to the one shown in FIG. 1.

In FIG. 3, there is shown an embodiment of the polymer coated packaging board 1 according to the invention, in which digitally printable EMA layers 3 are located on both sides of the fibre base 2. The materials and weights of the layers 2, 3 can be similar to the embodiment in FIG. 1.

FIG. 4 shows an embodiment of the invention in which the EMA layer 3 is located on the one side of the fibre base 2 and the LDPE heat sealing layer 6 on the opposite side. The fibre base 2 can consist of a three-layer board, as in the embodiment in FIG. 1. The EMA layer 3 consists preferably of copolymer, in which the share of methyl acrylate monomer is 15-20 mole percent. The weight of the EMA layer 3 can be between 7-20 g/$m^2$, and the weight of the LDPE layer 6 between 10-40 g/$m^2$. The board can be applied to digitally printable box packages to be sealed by seaming so that the edges of the packing blanks are brought to overlap in the seam points in order to heat seal the opposite EMA and LDPE layers to each other.

FIG. 5 presents the packaging board 1 coated with polymer on both sides, in which the fibre base 2 is provided with the EMA layer 3 on the one side, for example, as in FIG. 1. On the opposite side of the fibre base 2 there is arranged the oxygen and water vapour barrier 7 of ethyl vinyl alcohol copolymer (EVOH), the weight of which is, for example, 5-10 g/$m^2$, and further an outer LDPE heat sealing layer 6. The layer weight of the latter can be between 10-40 g/m . Such a coated board is suitable for box or can packages that are closed by seaming and digitally printed on the outer surface, in which the EVOH layer 7 remains on the inside of the fibre base of the package. The EMA layer 3 makes it possible to digitally print the outer side of the package at the same time as the EVOH barrier layer 7 in the interior of the package protects the packed product from the oxygen and moisture in the air.

Figure 1:
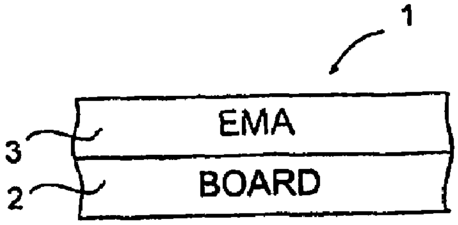
FIG. 1 presents a board according to the invention, with an EMA coating layer on the one side.
Figure 2:
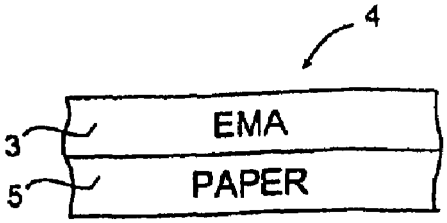
FIG. 2 presents a paper according to the invention, with an EMA coating layer on the one side.
Figure 3:
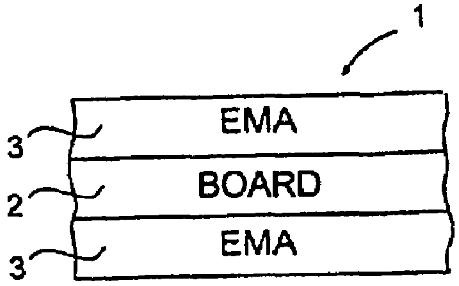
FIG. 3 presents a board according to the invention, with an EMA coating layer on both sides.
Figure 4:
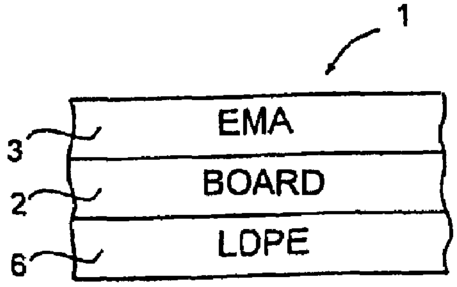
FIG. 4 presents a board according to the invention, with an EMA coating layer provided on the one side and a LDPE heat sealing layer on the opposite side.
Figure 5:
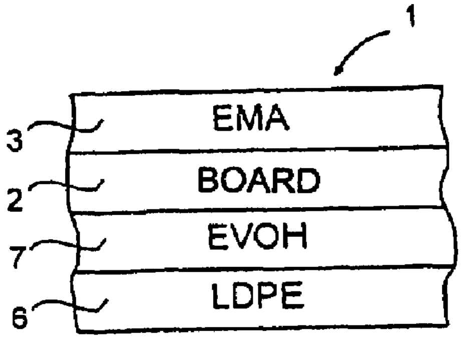
FIGS. 5-7 present boards according to the invention, coated with polymer on both sides and containing EVOH or PA barrier layers and LDPE heat sealing layers in addition to the EMA layer.
Figure 6:
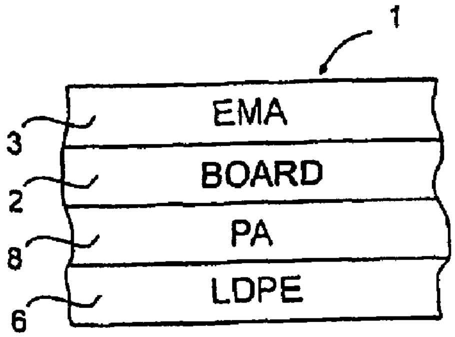
Figure 7:
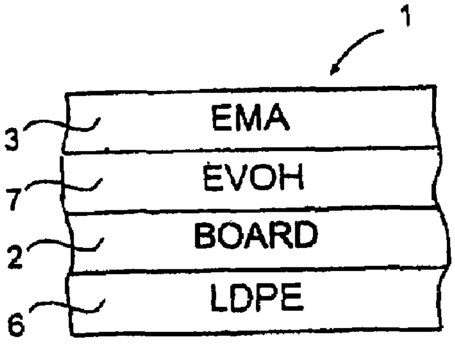

The embodiment of FIG. 6 differs from the one shown in FIG. 5 in that, instead of EVOH, the polymer of the barrier layer is polyamide (PA). In the embodiment of FIG. 7 the difference again is that the EMA and EVOH layers 3, 7 are placed against each other on the same side of the fibre base.

DETAILED DESCRIPTION OF THE INVENTION

The Charging of Different Polymers

The charging of different polymers was examined by films manufactured of them, to which corona treatment was first performed. This produces a permanent electric charge to the surface of the film and an opposite-signed charge to the interior of the film so that the film begins to act like a permanent magnet. After this, polar Porabak Q powder was poured onto the films, the powder consisting of ball-shaped polymer particles, the size of which is 80-100 mesh. The films were turned back and forth for spreading the powder, after which the extra powder not adhered to the film was removed by shaking carefully. The powder adhered to the surface of the film was viewed under a microscope.

Figure 8:
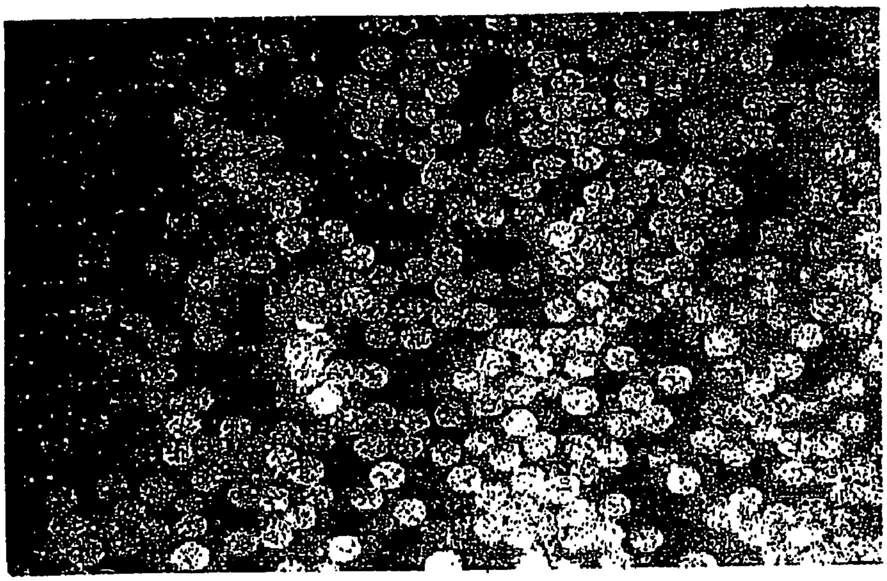
FIG. 8 presents powder particles photographed on EMA film.
Figure 9:
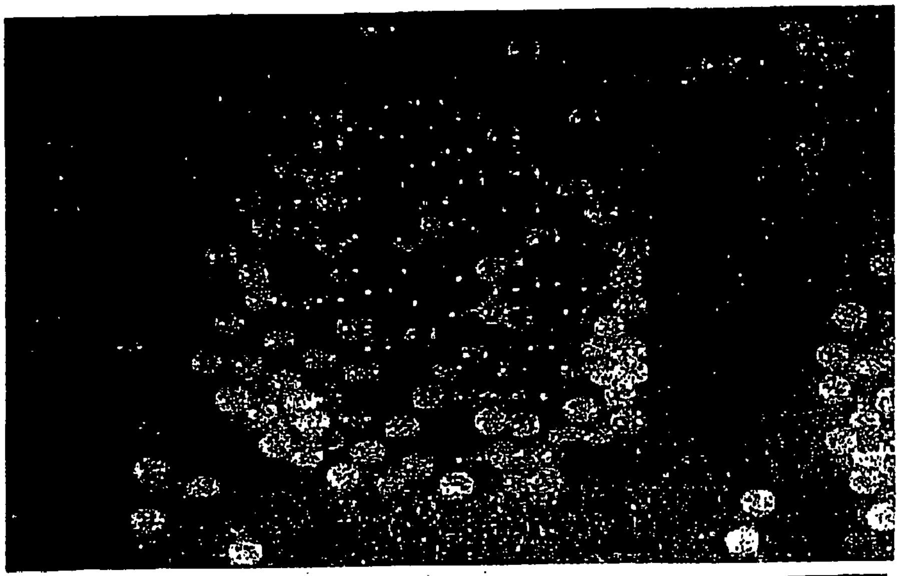
FIG. 9 presents powder particles photographed on PET film.
Figure 10:
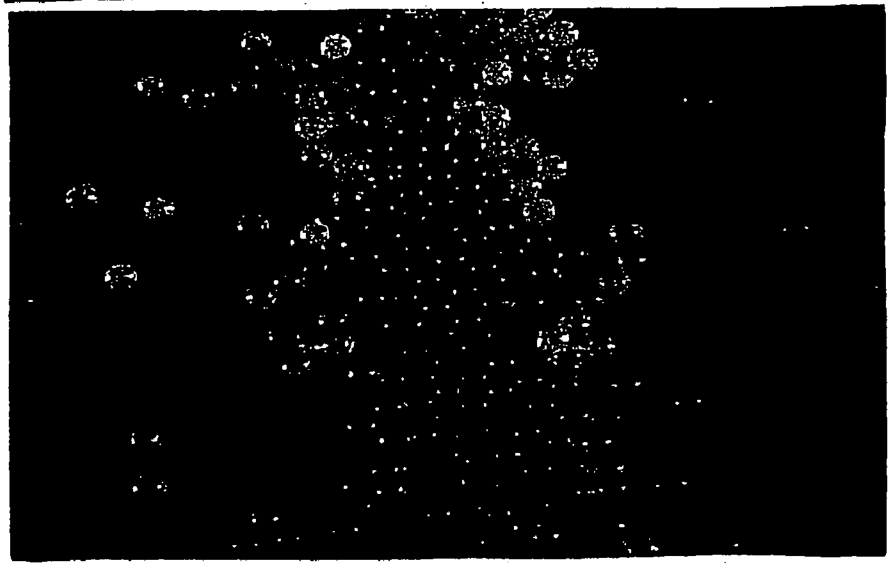
FIG. 10 presents powder particles photographed on LDPE film.

The examined polymers were EMA, in which the share of methyl acrylate monomer was 20 mole percent, PET and LDPE. It was found out that the most uniform and tight adhesion of the powder to the surface of the film was achieved with the EMA film. With the PET and LDPE films, the adhesion of the powder was considerably less uniform. Powder particles photographed on different polymer films are seen in the enclosed FIGS. 8 (EMA film) 9 (PET film) and 10 (LDPE film).

Digital Printability of Different Polymer Coatings

A series of tests was performed, in which cup board with the weight of 170 g/$m^2$ was coated with ten different polymers, the layer weight of which was 10-15 g/$m^2$. Each coating polymer was tested both subjected to a preliminary corona treatment and without such a corona treatment. Each of the 20 samples in all were printed using a technique according to the publication EP 629 930, and an examining board of ten persons assessed the results visually by listing the printed samples in order from best to worst so that the best sample was given the value 1 and the poorest sample the value 20. Of these values, averages and deviations have been calculated. In addition, the adhesion of the toner (%) after a fusion by IR radiation was measured twice from each sample. The results are shown in the following Table 1.

TABLE 1

| | Polymer | | | | | | | | | |
|---|---|---|---|---|---|---|---|---|---|---|
| | LDPE | | HDPE 8400 | | HDPE 9600 | | EMA 9% | | PP | |
| | Sample No | | | | | | | | | |
| Placing Assessor | 1 | 2 Corona | 3 | 4 corona | 5 | 6 corona | 7 | 8 corona | 9 | 10 corona |
| 1 | 12 | 20 | 17 | 18 | 14 | 10 | 7 | 19 | 11 | 9 |
| 2 | 12 | 19 | 20 | 18 | 17 | 11 | 9 | 5 | 8 | 10 |
| 3 | 17 | 18 | 8 | 20 | 12 | 19 | 14 | 13 | 3 | 10 |
| 4 | 8 | 11 | 4 | 17 | 6 | 18 | 20 | 15 | 13 | 12 |
| 5 | 10 | 16 | 8 | 15 | 11 | 17 | 12 | 9 | 3 | 4 |
| 6 | 15 | 14 | 7 | 16 | 8 | 17 | 20 | 4 | 18 | 11 |
| 7 | 17 | 16 | 19 | 20 | 14 | 18 | 11 | 9 | 5 | 4 |
| 8 | 12 | 14 | 15 | 20 | 16 | 19 | 17 | 18 | 3 | 13 |
| 9 | 14 | 16 | 17 | 20 | 19 | 18 | 13 | 12 | 5 | 11 |
| 10 | 13 | 14 | 17 | 20 | 18 | 19 | 16 | 15 | 6 | 7 |
| Average | 13.0 | 15.8 | 13.2 | 18.4 | 13.5 | 16.6 | 13.9 | 11.9 | 7.5 | 9.1 |
| Deviation | 2.9 | 2.7 | 5.8 | 1.9 | 4.3 | 3.3 | 4.4 | 5.1 | 5.0 | 3.1 |
| Adhesion of | 44 | ~100 | 9 | 98 | 8 | 91 | 98 | ~100 | 8 | 96 |
| the toner (%) | 50 | ~100 | 10 | 98 | 8 | 91 | 99 | ~100 | 6 | 88 |

| | Polymer | | | | | | | | | |
|---|---|---|---|---|---|---|---|---|---|---|
| | PET | | EVOH | | PA | | EMA20% | | SURLYN | |
| | Sample No | | | | | | | | | |
| Placing Assessor | 11 | 12 corona | 13 | 14 corona | 15 | 16 corona | 17 | 18 corona | 19 | 20 corona |
| 1 | 5 | 3 | 1 | 13 | 2 | 16 | 15 | 6 | 8 | 4 |
| 2 | 14 | 13 | 16 | 7 | 3 | 15 | 1 | 2 | 6 | 4 |
| 3 | 1 | 2 | 6 | 4 | 7 | 16 | 11 | 15 | 5 | 9 |

TABLE 1-continued

| | | | | | | | | | | |
|---|---|---|---|---|---|---|---|---|---|---|
| 4 | 16 | 3 | 9 | 7 | 19 | 14 | 1 | 2 | 10 | 5 |
| 5 | 13 | 2 | 14 | 7 | 20 | 19 | 1 | 6 | 18 | 5 |
| 6 | 12 | 1 | 3 | 2 | 19 | 13 | 6 | 10 | 5 | 9 |
| 7 | 7 | 1 | 10 | 8 | 15 | 13 | 3 | 2 | 12 | 6 |
| 8 | 7 | 1 | 8 | 2 | 11 | 6 | 4 | 5 | 9 | 10 |
| 9 | 15 | 1 | 10 | 9 | 8 | 4 | 3 | 2 | 7 | 6 |
| 10 | 8 | 1 | 10 | 4 | 12 | 11 | 2 | 3 | 9 | 5 |
| Average | 9.8 | 2.8 | 8.7 | 6.3 | 11.6 | 12.7 | 4.7 | 5.3 | 8.9 | 6.3 |
| Deviation | 4.9 | 3.7 | 4.5 | 3.4 | 6.6 | 4.6 | 4.7 | 4.3 | 3.9 | 2.2 |
| Adhesion of | 99 | ~100 | 96 | 96 | 92 | 92 | 98 | 98 | 97 | ~100 |
| the toner (%) | ~100 | | 96 | 96 | 88 | 94 | 97 | 99 | 98 | ~100 |

When assessing the impression, the best of the coatings not subjected to preliminary corona treatment proved to be EMA 20%, i.e. EMA, in which the share of methyl acrylate monomer was 20 mole percent. With the samples subjected to preliminary corona treatment, EMA 20% was placed second after PET. With EMA 20%, the adhesion of toner was 98%, i.e. very good. Due to its heat sealability, EMA 20% is especially suitable for packing applications.

Polymers not within the scope of the invention, which were included in the test as reference samples, proved to have poorer properties than EMA 20%, and most of them turned out to be insufficient for digital printing. Of the coatings subjected to preliminary corona treatment, polyethylene terepthalate was assessed to be the best concerning the impression. However, without the preliminary corona treatment, the result of PET remained average. Because the influence of coronation in the coating does not stay but disappears in time, in the practical applications, PET loses to the examined EMA 20%, whose permanent digital printing properties are better without the corona treatment. The drawback of PET in packing applications is also that it does not become heat sealed.

It is obvious for one skilled in the art that the embodiments of the invention are not limited to those presented above as examples, but they can vary within the scope of the following patent claims.

We claim:

1. A heat-sealable digitally printed paper or board comprising a paper or board base having a top and a bottom surface, and at least one extruded polymer coating directly adhered to the top surface of the paper or board base, and wherein an outermost wax free extruded polymer coating comprises an electrically chargeable acrylate copolymer of ethylene selected from a group consisting of ethylene methyl acrylate copolymer (EMA), ethylene ethyl acrylate copolymer (EEA), and ethylene butyl acrylate copolymer (EBA), and the outermost extruded polymer coating having a non-irregular top surface with fused toner particles forming a print image on the top surface.

2. The printed paper or board of claim 1, wherein the electrically chargeable acrylate copolymer of ethylene is ethylene methyl acrylate copolymer (EMA).

3. The printed paper or board of claim 2, wherein both top and bottom surfaces of the paper or board are coated with ethylene methyl acrylate copolymer (EMA).

4. The printed paper or board of claim 3, wherein the ethylene methyl acrylate copolymer (EMA) further comprises methyl acrylate monomer.

5. The printed paper or board of claim 4, wherein the methyl acrylate monomer comprises from about 9 mole percent to about 20 mole percent.

6. The printed paper or board of claim 5, wherein the methyl acrylate monomer comprises from about 15 mole percent to about 20 mole percent.

7. The printed paper or board of claim 1, wherein the board is packaging board and a weight of the packaging board is about 130 $g/m^2$ to about 500 $g/m^2$.

8. The printed paper or board of claim 7, wherein a weight of the packaging board is about 170 $g/m^2$ to about 300 $g/m^2$.

9. The printed paper or board of claim 1, wherein a weight of the paper is about 20 $g/m^2$ to about 130 $g/m^2$.

10. The printed paper or board of claim 8, wherein a weight of the paper is about 40 $g/m^2$ to about 120 $g/m^2$.

11. The printed paper or board of claim 1 wherein the electrically chargeable acrylate copolymer of ethylene is ethylene methyl acrylate copolymer, and a weight of the ethylene methyl acrylate copolymer coating is about 7 $g/m^2$ to about 20 $g/m^2$.

12. The printed paper or board of claim 1, wherein the outermost extruded polymer coating is directly adhered to the top surface of the paper or board base.

13. The printed paper or board of claim 12, wherein the electrically chargeable acrylate copolymer of ethylene is ethylene methyl acrylate (EMA).

14. The printed paper or board of claim 13, wherein ethylene methyl acrylate copolymer comprises the sole polymer coating adhered to the top surface of the paper or board base.

15. The printed paper or board of claim 14, wherein substantially pure ethylene methyl acrylate copolymer comprises the sole coating.

16. A method of digitally printing a paper or board, wherein the paper or board comprises a top and a bottom surface and at least one extruded coating layer directly adhering to the paper or board, and wherein an outermost wax free extruded polymer coating layer substantially comprises an electrically chargeable acrylate copolymer of ethylene selected from a group consisting of ethylene methyl acrylate copolymer (EMA), ethylene ethyl acrylate copolymer (EEA), and ethylene butyl acrylate copolymer (EBA), and the outermost extruded polymer coating having a non-irregular top surface, the method comprising the steps of:

providing the coated paper or board, wherein the outermost coating layer contains electrically chargeable acrylate copolymer of ethylene;

electrically charging a surface of the paper or board;

transferring toner particles to the surface of the paper or board by way of an electric field, wherein the toner particles form a print image; and directing infrared radiation to the toner particles on the paper or board surface thereby heat fusing the toner particles to the polymer coating.

17. A sealed box package comprising a packaging board configured into a package having an inside and an outside, the packaging board having an interior surface that relates to the inside of the package and exterior surface that relates to the outside of the package, and a wax free extruded polymer coating directly adhered to at least a portion of the exterior surface of the packaging board, wherein the polymer coating provides at least one heat-seal that seals the package, the polymer coating containing an electrically chargeable polymer selected from the group consisting of ethylene methyl acrylate copolymer (EMA), ethylene ethyl acrylate copolymer (EEA), and ethylene butyl acrylate copolymer (EBA), and the polymer coating having a non-irregular outer surface with fused toner particles forming a digitally printed image on the exterior of the package.

* * * * *